United States Patent
Genet et al.

(10) Patent No.: US 7,447,539 B2
(45) Date of Patent: Nov. 4, 2008

(54) METHOD AND EQUIPMENT FOR FIBER OPTIC HIGH-RESOLUTION, IN PARTICULAR CONFOCAL, FLUORESCENCE IMAGING

(75) Inventors: Magalie Genet, Guyancourt (FR); Bertrand Viellerobe, Nogent sur Marne (FR); Frederic Berier, Courbevoie (FR); Sophie Clade, Paris (FR)

(73) Assignee: Mauna Kea Technologies, Paris (FR)

( * ) Notice: Subject to any disclaimer, the term of this patent is extended or adjusted under 35 U.S.C. 154(b) by 514 days.

(21) Appl. No.: 10/521,607

(22) PCT Filed: Jul. 11, 2003

(86) PCT No.: PCT/FR03/02196
§ 371 (c)(1), (2), (4) Date: Jan. 18, 2005

(87) PCT Pub. No.: WO2004/008952
PCT Pub. Date: Jan. 29, 2004

(65) Prior Publication Data
US 2005/0242298 A1   Nov. 3, 2005

(30) Foreign Application Priority Data
Jul. 18, 2002   (FR)   ................. 02 09099
Mar. 11, 2003   (FR)   ................. 03 02972

(51) Int. Cl.
*A61B 1/06*   (2006.01)
(52) U.S. Cl. .............. 600/478; 600/160; 600/476
(58) Field of Classification Search .......... 600/478, 600/477, 476, 472, 160, 182, 199, 431, 407; 356/317; 385/115–117
See application file for complete search history.

(56) References Cited

U.S. PATENT DOCUMENTS 3,753,607 A   8/1973   Kitano et al.

(Continued)

FOREIGN PATENT DOCUMENTS

WO   WO 00/16151   3/2000

OTHER PUBLICATIONS

Knittel, J. et al.: "Endoscope-compatible confocal microscope using a gradient index-lens system", Optics Communications, North-Holland Publishing Co., Amsterdam, NL, vol. 188, No. 5-6, Feb. 15, 2001, pp. 267-273, XP-004317426.

(Continued)

*Primary Examiner*—Eric F Winakur
*Assistant Examiner*—Lawrence N Laryea
(74) *Attorney, Agent, or Firm*—Osha • Liang LLP (57) ABSTRACT

A method using an image guide having several thousands of optical fibers, an excitation signal emitted by a source, deflected and injected by turns into the optical fibers, each excitation point of the tissue in the fiber output emitting in return a fluorescence signal collected by the fiber, then detected and digitized to form an image element. The method focuses the beam in the fiber output to excite a subsurface plane to produce a confocal image. The production of a divergent beam in the fiber output can excite a micro-volume of the tissue from the surface. The method deflects the excitation signal at a speed corresponding to acquisition of a number of images per second sufficient for real time use and in detecting the fluorescence signal at a detecting frequency corresponding to a minimum frequency for sampling the fibers one-by-one.

25 Claims, 4 Drawing Sheets

U.S. PATENT DOCUMENTS

| | | | |
|---|---|---|---|
| 5,450,501 A * | 9/1995 | Smid | 382/260 |
| 5,672,880 A | 9/1997 | Kain | |
| 5,719,391 A | 2/1998 | Kain | |
| 5,737,121 A | 4/1998 | Dixon | |
| 5,813,987 A * | 9/1998 | Modell et al. | 600/473 |
| 6,061,591 A * | 5/2000 | Freitag et al. | 600/476 |
| 6,370,422 B1 * | 4/2002 | Richards-Kortum et al. | 600/478 |
| 6,400,487 B1 | 6/2002 | Harris et al. | |
| 6,748,259 B1 * | 6/2004 | Benaron et al. | 600/476 |
| 6,753,966 B2 * | 6/2004 | Von Rosenberg | 356/432 |
| 7,231,243 B2 * | 6/2007 | Tearney et al. | 600/407 |
| 2002/0045811 A1 | 4/2002 | Kittrell et al. | |
| 2004/0032650 A1 * | 2/2004 | Lauer | 359/385 |

OTHER PUBLICATIONS

Rouse, A.R. et al.: "Multispectral imaging with a confocal microendoscope", Optics Letters, Optical Society of America, Washington, D.C., vol. 25, No. 23, Dec. 1, 2000, pp. 1708-1710, XP-000981049.

* cited by examiner

METHOD AND EQUIPMENT FOR FIBER OPTIC HIGH-RESOLUTION, IN PARTICULAR CONFOCAL, FLUORESCENCE IMAGING

BACKGROUND OF THE INVENTION

1. Field of the Invention

The present invention relates to a method and apparatus for fibred high-resolution fluorescence imaging, in particular confocal imaging. The intended field of application is more particularly that of in vivo and in situ imaging.

2. Description of the Related Art

In the state of the art, the following fluorescence methods and apparatus have been described.

In an article in "Applied Optics", Vol. 38, No. 34, December 1999, pages 7133-7144, is presented a confocal microendoscope using a bundle of flexible optical fibres and equipped at its distal end with a miniature optical focussing head; it is provided to scan the bundle of optical fibres in lines, the apparatus comprising a detection slit as well as a CCD linear detector of the charge-transfer type. With an apparatus of this type 4 images/s can be obtained, which is too slow for in situ imaging dependent on the movement of the subject and of the operator. Moreover, the fact of scanning in lines and not point by point degrades the confocal character and leads to a less well resolved image.

In an article in "Optics Communication", 188 (2001), pages 267-273, is presented the coupling of a confocal laser scanning desktop microscope with a bundle of flexible optical fibres which is equipped at its distal end with a miniature optical head. The desired aim is to make the microscope compatible with an endoscope. The scanning is carried out fibre by fibre but the desktop microscope used is of standard design, designed to display a fixed specimen without concern for the time taken to obtain an image. An exposure time of 2 seconds is proposed in this article, much too long for a real-time in situ imaging.

SUMMARY OF THE INVENTION

The present invention aims to propose a method and apparatus for fibred high-resolution fluorescence imaging, in particular confocal imaging, of the type using an image guide made of optical fibres scanned one by one by an excitation beam emitted continuously, said method and apparatus making it possible to obtain the display in real time of a site in vivo and in situ, i.e. capable of providing a sufficient number of point by point images per second without being dependent on the movements of the subject and the operator in order to obtain in particular a fairly rapid examination.

An aim of the present invention is also to propose a method and apparatus which, in a general way, optimize the quality of each image in order to obtain in particular an excellent lateral and axial resolution.

According to a first feature of the invention, a method is proposed for the realization of a confocal fluorescence in vivo and in situ image, the method using an image guide made of several thousands of optical fibres and consisting of the point by point scanning of a tissue in a subsurface plane, each point corresponding to an excitation signal emitted by a continuous source, deflected and injected into one of the optical fibres of said bundle then focused on the exit of said fibre in said plane, each point emitting in return a fluorescence signal collected by said optical fibre, then detected and digitized to form an image element, characterized in that the excitation signal is deflected at a speed corresponding to acquisition of a number of images per second sufficient for a real-time use and in that the fluorescence signal is detected at a detection, frequency corresponding to a minimum sampling frequency of the fibres one-by-one.

The fluorescence observed may come from an exogenous compound (typically an injected marker) or an endogenous compound (present in the cell) of a biological tissue.

More particularly, the method of confocal imaging according to the invention is of the type which consists of scanning a tissue point by point in a subsurface plane, each point corresponding to an excitation signal emitted by a continuous source, deflected and injected by turns into an optical fibre of a bundle of optical fibres, then focussed at the exit of said fibre in said plane, each point emitting in return a fluorescence signal collected by said optical fibre, then detected and digitized to form an image element.

The confocal character is obtained using the same optical path, in particular the same optical fibre which is used for spatial filtering, to transport the excitation signal and the fluorescence signal emitted in response, and using an optical system adapted to conjugate the focussing point in the tissue with said optical fibre.

The corresponding confocal imaging apparatus comprises the bundle of flexible optical fibres (usually called image guide) with, at its proximal end:

the source emitting continuously or in pulsed mode at the excitation wavelength of one or more targeted fluorophores, typically a laser source;

means for rapid scanning over time of the excitation beam produced by the source in lines and columns in a XY plane corresponding to the entry section of the image guide;

means for injecting the excitation beam into one of the optical fibres;

means for detecting the fluorescence signal; and control means, in particular for the scanning means.

Means are also provided adapted for the realization and the display of an image from the signals successively detected on each fibre.

At the distal end of the image guide in an optical head, intended to be brought into contact with the observed tissue, allowing the excitation beam to be focused at a given depth) tens of µm) and thus the realization of a subsurface image.

In practice, this type of apparatus has the following advantages in particular:

on the distal side of the image guide there is only one focusing optic, which is less fragile and less costly than an optical head with incorporated scanning means, the replacement of the optical head being able to be envisaged independently of the scanning means; moreover the head can be miniaturized, which is advantageous in endoscopy and also, in a general way, for increasing the precision of positioning;

an image guide made of flexible optical fibres, serves as an access arm to the site to be observed, which is important for an in situ application.

According to a second feature of the invention, a method is proposed for the realization of a high-resolution fluorescence image using an image guide made of several thousands of optical fibres, an excitation signal being emitted by a continuous source, deflected and injected by turns into one of the optical fibres of said image guide and a fluorescence signal emitted in response being collected by the same optical fibre as the one used for the excitation, then detected and digitized to form an image element, characterized in that the end of the fibres is intended to be placed bare directly in contact with the surface of the tissue to be imaged, each fibre being adapted to produce a divergent beam which is adapted to excite a microvolume of the tissue situated at the surface to a maximum depth depending in particular on the core diameter of the optical fibres and in that the excitation signal is deflected at a speed corresponding to acquisition of a number of images per second sufficient for a real-time use and in that the fluorescence signal is detected at a detection frequency corresponding to a minimum sampling frequency of the fibres one-by-one.

This method thus differs from the method according to the first feature in that it does not provide the scanning of a signal which is focussed on the exit of each fibre but the scanning of a divergent signal on the exit of each fibre. The non-focussing of the signal on the exit of the fibre makes it possible to obtain images of a volume situated just beneath the surface of the tissue, images which can be processed and which are advantageous in particular from a medical point of view. These images are not "confocal" because they do not originate from a subsurface section plane that has been scanned point by point, but images which can nevertheless be called "high-resolution" because they come from the scanning by turns of microvolumes situated directly beneath the surface and from a spatial filtering of the fluorescence signal emitted by each microvolume by the same fibre as the one which was used for the excitation. The main advantage of such an apparatus resides in the fact, that for an endoscopic application, the diameter of the endoscopic probe can be very small depending solely on the diameter of the image guide and therefore on its number of optical fibres. This allows fields of application to be envisaged, such as for example the field of neurology, where the size of the endoscopic probe is a critical factor in overcoming the problems inherent in the miniaturization of the optical focussing head.

The present invention proposes a solution for realizing an in vivo and in situ image in real time, whether for a method with or without focusing on the exit of the fibre. The invention is based on respecting the sampling of the fibres (according to Shannon's criterion) which makes it possible to obtain an image reconstructed point by point which effectively corresponds to each fibre. This avoids loss of information when sampling all of the fibres on by one while still maintaining a minimum average number of images per second, i.e. in practice at least 12 images per second for a maximum mode of 640×640 pixels. The choice of detection frequency (passband of the detector) as a function of this minimum sampling then allows the detection, for each fibre, of the greatest possible number of fluorescence photons.

Thus, according to a possible embodiment, using an image guide with approximately 30 000 flexible optical fibres, the sampling frequency and the pass-band of the detection system (an avalanche photodiode or equivalent) are fixed at approximately 1.5 MHz, corresponding approximately to 12 pixels per fibre, thus allowing as a minimum the 12 images/s in maximum mode 640×640 pixels to be obtained.

In practice, according to an advantageous embodiment, which makes it possible an appropriate rapid scanning of the fibres in order to obtain a real-time image, the deflection of the beam is adjusted by determining a rapid-resonance frequency of a resonating "line" mirror and a slow-resonance frequency of a galvanometric "frame" mirror.

According to the invention, the detection period for a flux coming out from a fibre is time-limited and is very short to respect the acquisition of a real-time image. According to the invention, optimization means have thus also been provided to collect and detect the maximum flux coming from the specimen during this limited detection period, in particular:

optical deflection, injection, if appropriate focussing and detection means are used presenting a degree of achromaticity which depends on the wavelength difference between the excitation wavelength and the maximum fluorescence wavelength, as well as on the spectral width of the emitted fluorescence signal; this advantageously allows optimization of the fluorescence flux collected over the whole of the spectral band of emitted fluorescence;

if appropriate, a numerical aperture of the focussing optics on the tissue comprised between approximately 0.5 and 1 is chosen, which makes it possible to achieve a good compromise between the field size and the quantity of photons collected; and a detector is chosen having a quantum efficiency at the fluorescence wavelengths to be detected of at least 50%.

According to the invention, the image processing then carried out on the detected flux is also optimized, in order to obtain an image of very good quality from this limited flux of detected photons. This optimization is carried out in the following way.

A series of steps is carried out prior to the acquisition of images in real time:

a step of detection of the location of each fibre of a chosen set of fibres intended to be used (either all of the image guide or a chosen sub-set); this step is to be carried out at least at each change of image guide;

a step of calibrating the rate of injection into each fibre, i.e. of defining a rate of injection particular to each fibre; and a step of detection of the background image (without specimen).

During operation, the optimization of the image processing comprises in particular the steps consisting, after digitization of the detected signal, of:

defining the real flux collected by each fibre, i.e. only coming from the specimen, after correction as a function of the rate of injection particular to the fibre and subtracting the background image, so as to obtain a corrected signal;

then undertaking a reconstruction of the image from this corrected signal, in particular with the aim of transforming an image showing a mosaic of fibres in an image without apparent fibres.

According to the invention, these last two steps must be able to be carried out in real time. As regards the correction of the signal, this can take place in real time thanks to a processing which is suited to the structure of the observed signal and an optimized algorithm. As regards the reconstruction of the image, this can take place by choosing a number of operations per pixel which can be carried out in real time allowing the desired result to be achieved in terms of image quality. A Gaussian low-pass filtering represents a good compromise between the complexity of the processing, the quality of the result and the calculation time.

In order to save time and to increase the complexity of the processing corresponding to the reconstruction of the image, the processing capacity of the equipment can also be increased, for example by using a specific processing card and/or a parallel architecture such as a multiprocessor.

The present invention also proposes an apparatus adapted for the implementation of the method according to the first feature recited above, comprising:

the image guide;

the source emitting continuously at the excitation wavelength of at least one targeted fluorophore, means for rapid scanning and for injection fibre by fibre over time of the excitation beam produced by the source by lines and by columns in a XY plane corresponding to the entry section of the image guide;

means for separating the excitation wavelength and the fluorescence wavelengths;

means for detection of the fluorescence signal; and means for processing the detected signal allowing the realization of an image;

an optical head being arranged at the distal end, intended to be brought into contact with the observed tissue, allowing the excitation beam to be focussed.

The apparatus is characterized in that:

the scanning means are suitable for moving the excitation beam at a speed corresponding to the obtaining of an image in real time; and the detection means have a pass-band whose frequency is fixed as a function of the minimum sampling frequency of the fibres one-by-one.

The present invention also proposes an apparatus for the implementation of the method according to the second feature, comprising:

the image guide;

the source emitting continuously at the excitation wavelength of at least one targeted fluorophore, means for scanning and fibre-by-fibre injection of the excitation beam produced by the source in a XY plane corresponding to the entry section of the image guide;

means for separating the excitation wavelength and the fluorescence wavelengths;

means for detecting the fluorescence signal; and means for processing the detected signal allowing the realization of an image;

characterized in that the end of each fibre is suitable for producing a beam which is divergent and is intended to be placed bare directly in contact with the surface of the tissue to be observed;

and in that the scanning means are suitable for moving the excitation beam at a speed corresponding to the obtaining of an image in real time and the detection means have a pass-band whose frequency is fixed as a function of the minimum sampling frequency of the fibres one-by-one.

BRIEF DESCRIPTION OF THE DRAWINGS

The present invention will be better understood and other advantages will become apparent in the light of the following description of an embodiment, with reference to the attached drawings in which.

DETAILED DESCRIPTION OF THE PREFERRED EMBODIMENTS

Figure 1:
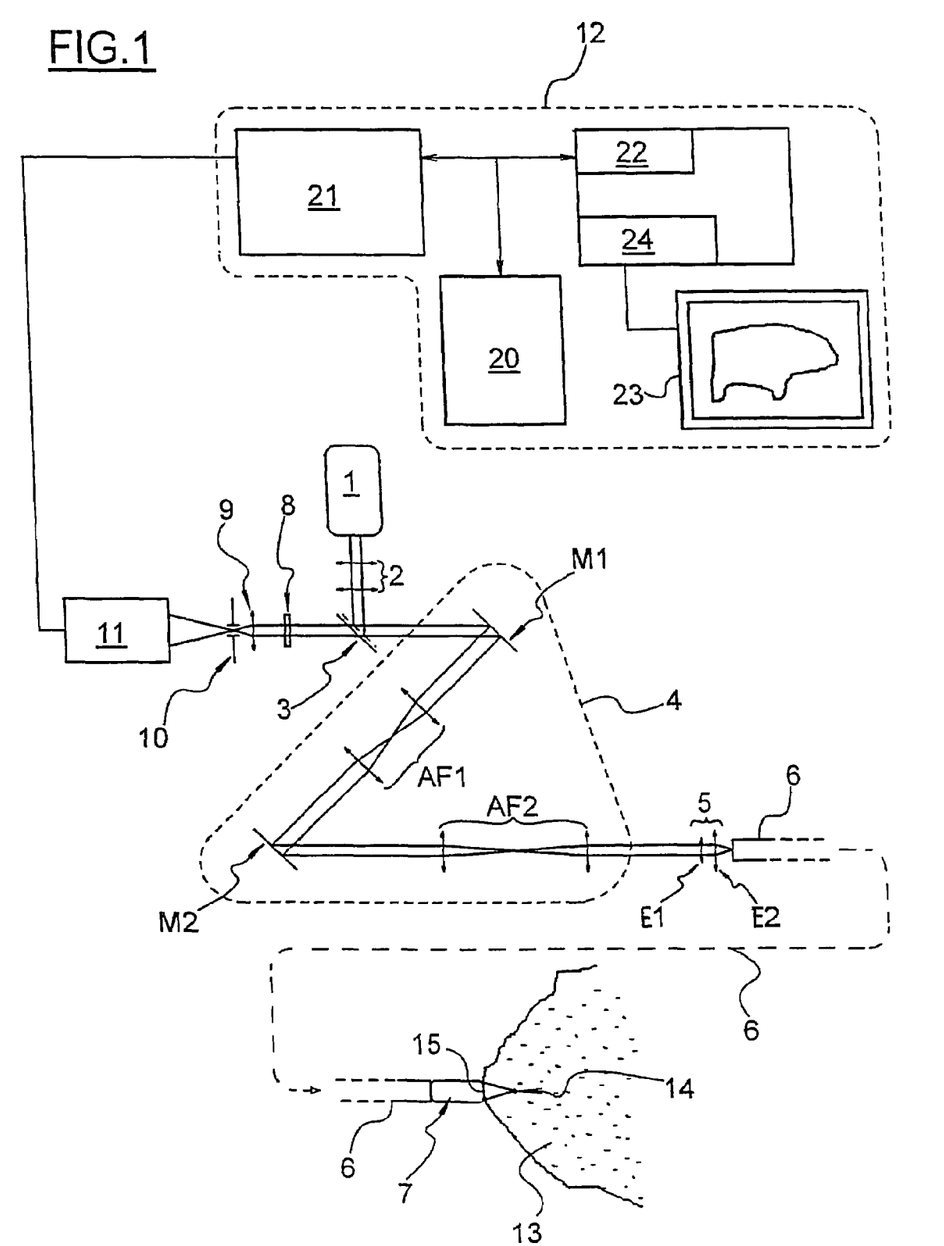
FIG. 1 schematically represents an embodiment of apparatus for confocal fluorescence imaging including a focussing head.
Figure 2:
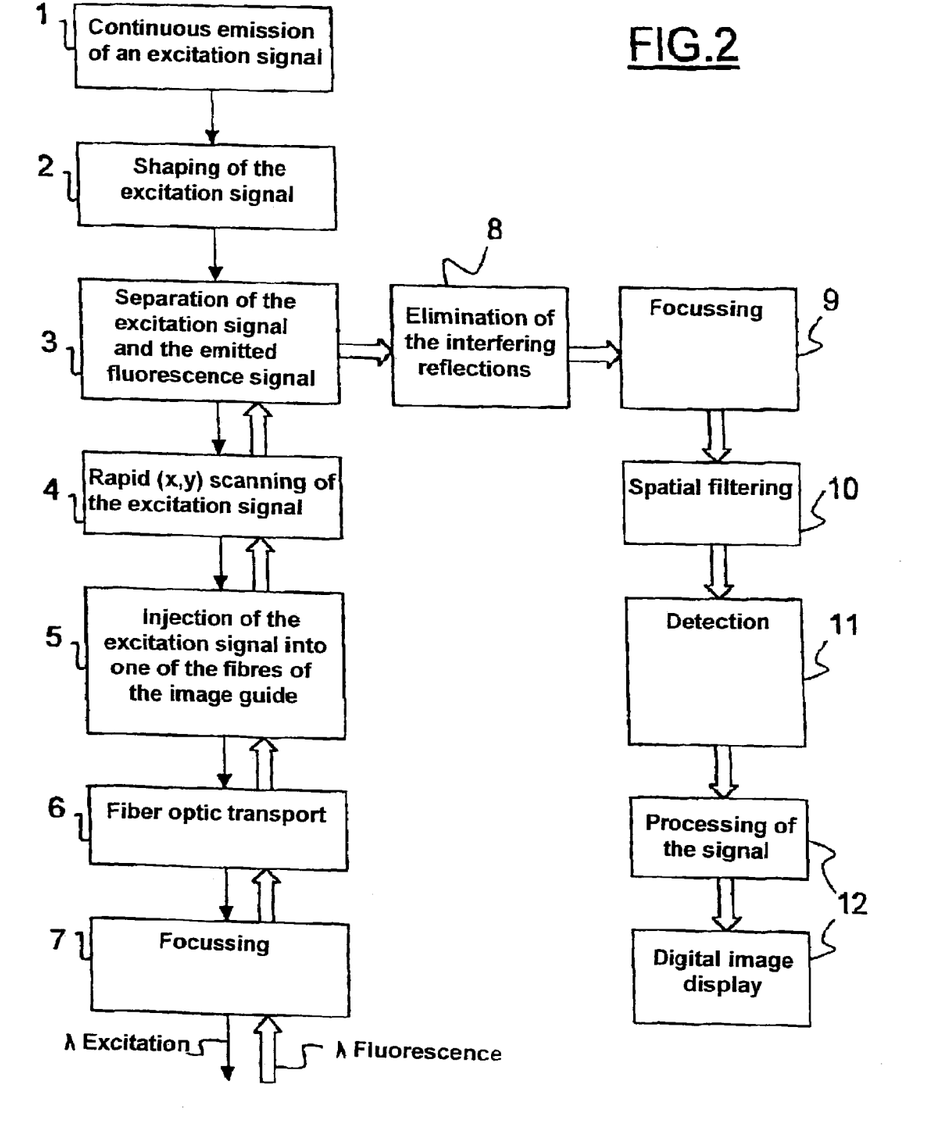
FIG. 2 is a block diagram of the apparatus of FIG. 1.

According to the example chosen and represented in FIGS. 1 and 2, the apparatus comprises:

a light source 1;

means 2 for shaping the excitation beam;

means 3 for separating wavelengths;

scanning means 4;

beam injection means 5;

an image guide 6 made up of flexible optical fibres;

an optical focussing head 7;

means 8 for rejecting the excitation beam;

means 9 for focussing the fluorescence signal;

means 10 for spatial filtering of the fluorescence signal;

means 11 for detecting the fluorescence signal; and means 12 for electronic and computer processing of the detected fluorescence signal and for display.

These different elements are detailed below.

The light source 1 is a laser emitting at an excitation wavelength allowing a wide range of fluorophores to be excited, for example 488 nm. In order to optimize the injection into one of the fibres of the image guide 6, the excitation beam is circular in order to be able to inject a fibre with a section which is also circular and, in order to optimize the rate of injection, the laser is preferably of the longitudinal monomode type in order to present the best possible wave front for the injection into a slightly multimode optical fibre. The laser emits continuously or in pulsed mode, and in a stable way (the smallest possible noise, <1%). The available output power is of the order of 20 mW. By way of example, a quantum well laser (VCSEL), a diode-pumped solid-state laser, a laser diode or a gas, such as argon, laser can be used.

The means 2 for shaping the excitation laser beam are placed on the exit of the source 1. They are made up of an afocal optical system of a magnification other than 1, comprising two lenses L1 and L2 which are adapted to modify the diameter of the laser beam. The magnification is calculated so that the diameter of the beam is suitable for the means 5 of injection into a fibre.

The shaped excitation laser beam is then directed towards the means 3 provided for separating the excitation and fluorescence wavelengths. It is for example a dichroic filter with a transmission efficiency of 98 to 99% of the excitation wavelength and which thus reflects substantially the other wavelengths. The fluorescence signal, which on the return follows the same optical path as the excitation signal (confocal character), will thus be almost totally sent towards the detection path (8-11). The rejection means 8 placed on the detection path serve to totally eliminate the 1 to 2% of interfering reflections at the excitation wavelength 488 nm which pass towards the detection path (for example a rejection filter at 488 nm, a band-pass filter allowing a transmission for example only between 500 and 600 nm, or a high-pass filter which allows a transmission above 500 nm).

The scanning means 4 then pick up the excitation beam. According to the example chosen and represented in FIG. 1, these means comprise a mirror M1 resonating at 4 KHz which serves to deflect the beam horizontally and thus to realize the lines of the image, a mirror M2 which is galvanometric at 15 Hz which serves to deflect the beam vertically and thus to realize the frame of the image; and two afocal systems with unitary magnification, AF1 situated between the two mirrors and AF2 situated after the mirror M2, these afocal systems being used to conjugate the rotation planes of the two mirrors M1 and M2 with the injection plane in one of the fibres. According to the invention, the scanning speed is determined in order to allow a real-time in vivo in situ observation of the tissues. For this, the scanning must be fast enough for there to be at least 12 images displayed on the screen for a display mode of 640×640 pixels corresponding to the slowest mode. For display modes with fewer pixels, the number of images acquired per second will thus always be greater than 12 images/s. By way of a variant, the scanning means can in particular comprise a rotating mirror, integrated components of the MEMs type (X and Y scanning mirrors), or an acousto-optical system.

The excitation beam deflected on the exit of the scanning means is directed towards the optical means 5 in order to be injected into one of the fibres of the image guide 6. These means 5 are in this case made up of two optical units E1 and E2. The first optical unit E1 is adapted for correction of part of the optical aberrations at the edge of the field of the scanning means 4, the injection thus being optimized over the whole optical field (at the centre as well as at the edge). The second optical unit E2 is intended to carry out the actual injection. Its focal length and its numerical aperture were chosen to optimize the rate of injection into the optical fibres of the guide 6. According to one embodiment which makes it possible to obtain the achromaticity criterion, the first unit E1 is made up of a doublet of achromatic lenses, and the second unit E2 of two doublets of achromatic lenses followed by a lens situated close to the image guide. By way of a variant, this injection optic could be made up of any other type of standard optics, such as for example two triplets, or index gradient lenses or a microscope lens (which is more costly however).

The image guide 6 is made up of a very large number of flexible optical fibres (several tens of thousands), for example 30 000 fibres of 2 μm in diameter and spaced 3.3 μm apart. In practice, the whole set of fibres of the image guide, or a chosen sub-set of these fibres, for example centred, can be used.

On the exit of the optical fibre, the excitation laser beam is focussed by the optical head 7 in the specimen 13 to a point 14 situated at a given depth situated between some tens of μm and about one hundred μm, relative to the surface 15 of the specimen with which the optical head is intended to be placed in contact. This depth can be for example 40 μm. The optical head thus allows focussing of the flux exiting the image guide in the specimen, but also collection of the fluorescence flux returning from the specimen. The optical head has a magnification of 2.4 and a numerical aperture on the specimen of 0.5. These two parameters are chosen so that the return signal occurs only in the optical fibre which has transmitted the excitation signal and not in adjacent fibres and to thus preserve the confocal filtering using one fibre. With these magnification and numerical aperture values, the axial resolution is of the order of 10 μm and the lateral resolution of the order of 1.4 μm. The numerical aperture is also chosen so as to optimize the number of photons recovered, which must be as large as possible. The optical head can be made up of standard optics (doublet, triplet, aspheric) and/or index gradient (GRIN) lenses and/or diffractive lenses, presenting an optical quality and chromatics suited to confocality, i.e. minimizing the optical aberrations, which would otherwise conduct in particular to degradations over the depth of field and consequently to the axial resolution of the apparatus. During operation, the optical head is intended to be placed in contact with the specimen 13. The latter is a biological tissue or a cell culture. The expression of the fluorescence is realized either by a fluorophore which is injected (systemic fluorescence), or by a fluorophore produced by the cell itself by modification of a gene (transgenic fluorescence). In both cases, the fluorophore re-emits photons over a spectral band of greater or lesser width which can range from some ten nanometers to more than one hundred nanometers.

On the detection path, the fluorescence signal, exiting the rejection filter 8, is then focussed by means 9, made up for example of a detection lens, in a filtering hole of the spatial filtering means 10. The focal distance of the detection lens is calculated so that the fluorescence signal coming from a fibre is the same size as or slightly smaller than the filtering hole. The latter allows the preservation of the fluorescence light coming only from the fibre illuminated by the incident beam. It allows rejection of the light which may have been coupled in the fibres adjacent to that which is illuminated. The size of the hole is calculated so that the image of a fibre fits into it perfectly. In this case, it is 20 μm. Moreover, still with a view to optimizing the quantity of photons passing through the filtering hole, and thus the detected flux, the scanning means 4, the injection means 5, the focussing means 7 of the optical head, and the detection means 8, 9 and 10 are adapted to the detected fluorophore: these means are chosen to be sufficiently achromatic to collect photons over the broadest fluorophore emission band.

The detection means 11 have a maximum sensitivity at the fluorescence wavelengths studied. An avalanche photodiode (APD) or a photomultiplier can be used for example. Moreover, according to the invention, the pass-band is chosen in order to optimize the integration time of the fluorescence signal. It is 1.5 MHz, which corresponds to the minimum sampling frequency of the image guide with an optimized integration time on each pixel.

The electronic and computer means 12 for control, analysis and digital processing of the detected signal and for display comprise the following cards:

a synchronization card 20 which serves:
  to control in a synchronized way the scanning, i.e. the movement of the line M1 and frame M2 mirrors;
  to know at any moment the position of the laser spot thus scanned; and
  to manage all the other cards via a microcontroller which can itself be piloted;
a detector card 21 which comprises an analogue circuit which in particular carries out an impedance match, an analogue-to-digital converter then a programmable logic component (for example an FPGA circuit) which shapes the signal;
a digital acquisition card 22 adapted to the processing of a flux of digital data at variable frequency and its display on a screen 23;
a graphics card 24.

By way of a variant, a single card can be used which combines the functionalities of these different cards.

The image processing takes place in the following way.

When an image guide is placed in the apparatus, a first operation is carried out to recognize the design of the fibres in the image guide, and thus to learn the real location of each fibre intended to be used.

The following operations are also carried out before the apparatus is used:
  determination of the rate of injection particular to each fibre, using a homogeneous specimen, this rate of injection being able to vary from one fibre to another; and
  measurement of the background image, carried out without a specimen.

These two operations can be carried out regularly as a function of the frequency of use of the apparatus. The results obtained will be used for correction in operation of the digital signal on the exit of the detector card.

During operation, according to the invention 2 processing groups are carried out on the digital signal on the exit of the detector card:

The first group consists in a first step of correcting the digital signal in particular in order to take account of the real rate of injection particular to the fibre from which said signal has come and in order to subtract from it the part of the flux corresponding to the background image. This allows processing of only a signal which really corresponds to the specimen observed. For this processing group a standard calculation algorithm is used which can be optimized in order to respect the constraint of real time.

The second group then comprises the reconstruction, from the corrected signal, of the digital image which will be displayed by the practician. The aim of the processing carried out is to provide for display a reconstituted digital image which is not simply a mosaic of image elements each corresponding to a corrected digital signal of a fibre placed side by side, but to provide a reconstituted digital image which no longer shows the fibres. An algorithm is used for this which is intended to carry out a certain number of operations on each pixel, the algorithm being chosen so as to observe the constraint of real time, i.e. it must represent a good compromise between the complexity of the operations required, the quality of the result that can be obtained and the calculation time. By way of example, a Gaussian low-pass filtering algorithm can be used.

The apparatus operates as follows. The source 1 produces a circular parallel excitation beam at a wavelength of 488 nm, which is then shaped in the afocal system 2 in order to give it the appropriate size for the best possible injection into the core of a fibre. This beam is then sent to the dichroic separation system 3 which reflects the excitation wavelength. The incident beam is then deflected angularly over time in two directions in space by the optomechanical scanning system of mirrors 4, and injected using optical injection means 5 into one of the fibres of the image guide 6. The electronic means 12 serve to control the injection of one of the optical fibres of the image guide at a given moment angularly deflecting the beam by means of the mirrors, point by point for a given line, and line after line, in order to constitute the image. On the exit of the guide, the light emerging from the injected fibre is focussed in the specimen by the optical head 7 at a point situated at a given depth situated between approximately some tens of μm and around one hundred μm. Thanks to the scanning, the specimen is illuminated point by point. At each moment, the spot illuminating the tissue thus emits a fluorescence signal which has the particularity of being shifted towards greater wavelengths. This fluorescence signal is picked up by the optical head 7, then follows the reverse path of the excitation beam to the dichroic filter 3 which will transmit the fluorescence signal to the detection path. The interfering reflections which form at the excitation wavelength will then be rejected by the rejection filter 8. Finally, the fluorescence signal is focussed in the filtering hole 10 in order to select only the light coming from the excited fibre and the photons are detected by the avalanche photodiode 11. The detected signal is then digitized and corrected. The detected signals, one after the other, are processed in real time using the image processing described above in order to allow the reconstruction of an image in real time displayed on the screen.

Figure 3:
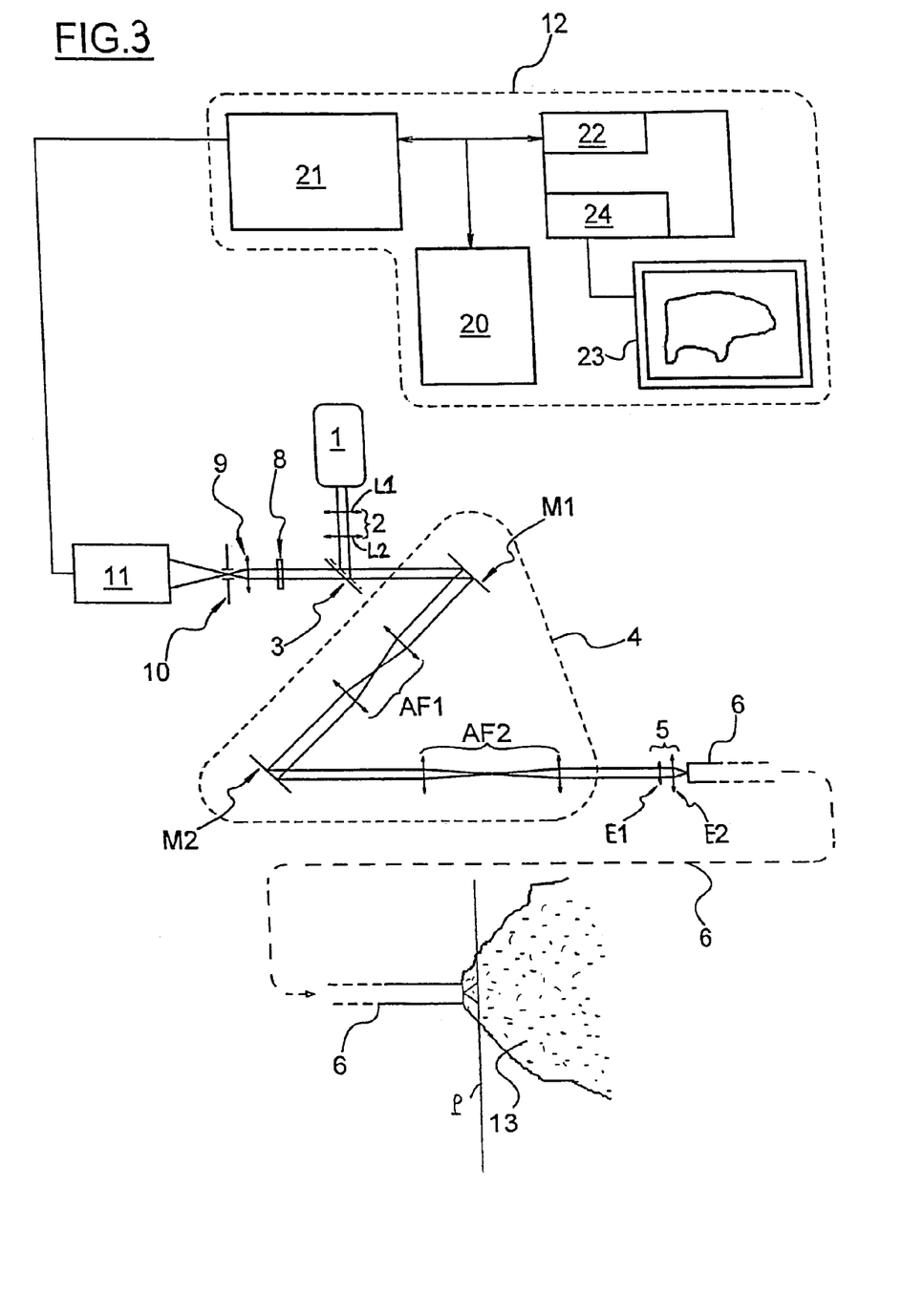
FIG. 3 schematically represents an embodiment of apparatus for high-resolution fluorescence imaging.
Figure 4:
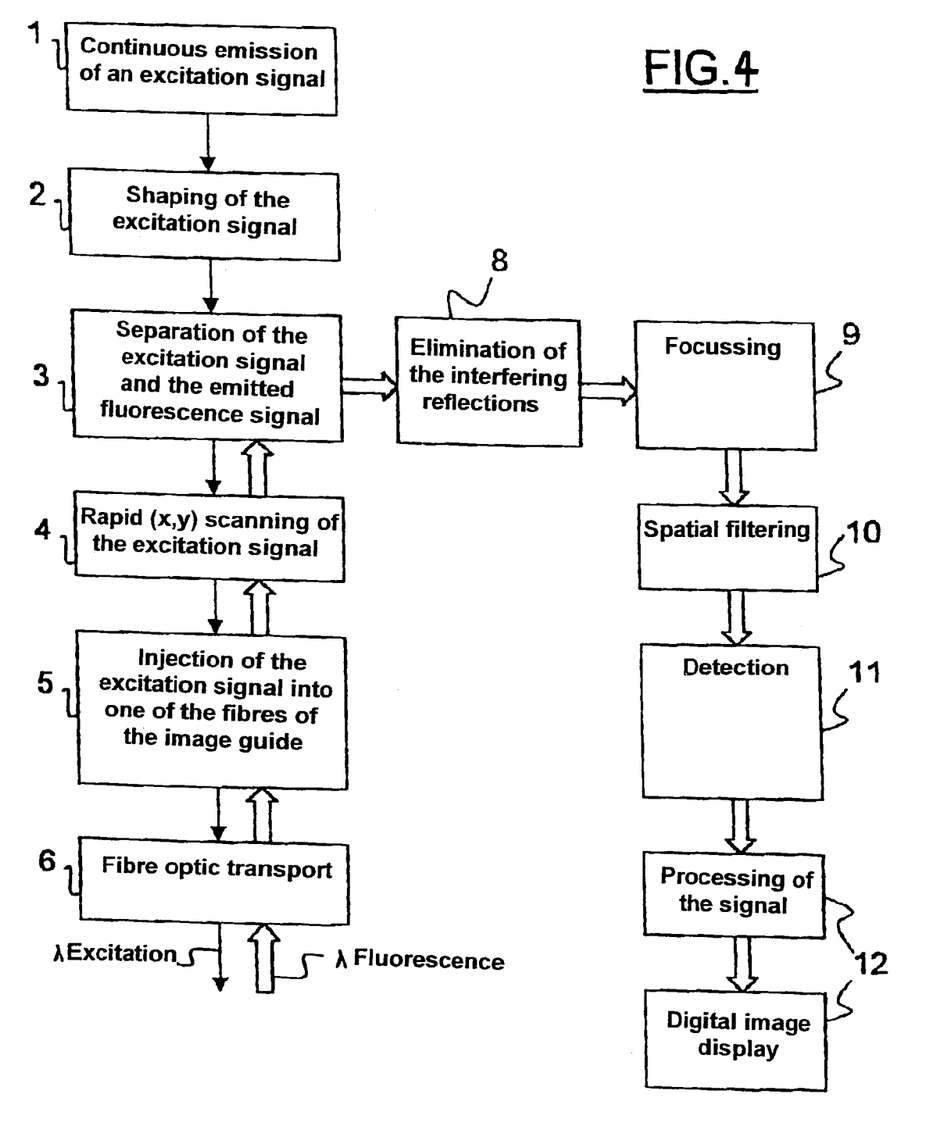
FIG. 4 is a block diagram of the apparatus of FIG. 3.

According to the embodiment selected and represented in FIGS. 3 and 4, the apparatus comprises the same elements as the apparatus of FIGS. 1 and 2 with the exception of the optical focussing head 7. The same reference numbers are used for these same elements in the figures and therefore will not be described again here in detail.

The image guide 6 used for this apparatus can be made up of approximately 5000 to 100 000 flexible optical fibres, depending on the external diameter of the guide which is sought, which is itself a function of the intended application (endoscopy, desired field size, etc.). For example they may be image guides marketed by FUJIKURA. The core diameter of the fibres is preferably between 1 and 4 μm. This leads to a beam divergence on the exit of the fibre presenting an angle of approximately 18° for a numerical aperture of 0.42 in the air.

A core diameter of 1 μm can be obtained by a method of stretching the end of the entire image guide. The end of the guide 6 is polished and does not contain optical means. The aim of the polishing is to give the surface of the guide, and thus the bare fibres in contact with the tissue, the same surface condition in order that on the one hand the obtained image background is as homogeneous as possible and, on the other hand, to suppress any problems of adherence of the fibres to the tissue, which would damage it. The polishing can be smooth or rounded in order to follow the shape of the tissue. The numerical aperture of each optical fibre is preferably chosen to be as large as possible in order to collect the maximum of fluorescence photons, i.e. for example 0.42. The intercore distance gives the lateral resolution of the image obtained (distance between two points of the image). The smaller this distance, the better the resolution will be, but this will be to the detriment of the size of the field to be imaged. A good compromise should thus be found between the number of fibres of the guide and the intercore distance between the fibres in order to obtain a good lateral resolution (between 2 and 8 μm) with a suitable field size for observing the tissue elements desired.

Two examples of guides which may be suitable according to the invention are given below:

|  | Example 1 | Example 2 |
|---|---|---|
| Number of fibres | 6,000 | 30,000 |
| Diameter of the imaged field | 300 μm | 650 μm |
| External diameter of the guide | 330 μm | 750 μm |
| Core diameter of a fibre | 3 μm | 1.9 μm |
| Intercore distance | 4 μm | 3.3 μm |
| Maximum integration depth of the signal from the surface (shown schematically by the plane P in FIG. 1) or axial resolution | 15-20 μm | 10-15 μm |
| Lateral resolution | 4 μm | 3.3 μm |

During operation, the distal end of the image guide is brought into contact with the specimen 13, the end surface of the fibres thus being directly in contact with the surface of the tissue. The latter is a biological tissue or a cell culture. The expression of the fluorescence is realized either by a fluorophore which is injected (systemic fluorescence), or by a fluorophore synthesized by the cell itself by modification of a gene (transgenic fluorescence). In both of these cases, the fluorophore present in the microvolume excited according to the invention re-emits photons over a spectral band of greater or lesser width which can range from some ten nanometers to more than one hundred nanometers.

The operation of the apparatus is the same as that described previously with the following exception: on the exit of the guide, the divergent light emerging from the injected fibre is diffused in the specimen and the fluorescence signal is collected in a microvolume situated between the surface and a maximum depth of 25 μm (depending on the core diameter of the fibres and their NA). Thanks to the screening, the specimen is illuminated microvolume by microvolume. At each moment, the microvolume excited in the tissue thus emits a fluorescence signal which has the particularity of being shifted towards greater wavelengths. This fluorescence signal is picked up by the same optical fibre as the one which was used for the excitation, then follows the reverse path of the excitation beam to the dichroic filter 3 which will transmit the fluorescence signal to the detection path. The detected signals are processed in real time, one after the other, using the same image processing as that described above with reference to FIGS. 1 and 2 in order to allow the real-time reconstruction of an image displayed on the screen.

The invention claimed is:

1. A method for realization of a confocal fluorescence in an in vivo and in situ image, comprising:
    employing an image guide made of several thousands of optical fibres; and
    point by point scanning of a tissue in a subsurface plane, each point corresponding to an excitation signal emitted by a continuous source, deflected and injected into one of the optical fibres of a bundle then focussed on an exit of said fibre in said plane, each point emitting in return a fluorescence signal collected by said optical fibre, then detected and digitized to form an image element, wherein the excitation signal is deflected at a speed corresponding to acquisition of a number of images per second sufficient for a realtime use and in that the fluorescence signal is detected at a detection frequency corresponding to a minimum sampling frequency of the fibres one-by-one.

2. The method according to claim 1, wherein a numerical aperture of the focussing optics is between approximately 0.5 and 1.

3. The method according to claim 1, wherein the deflection speed of the excitation beam is adjusted by determining a rapid-resonance frequency of a resonating line mirror and a slow-resonance frequency of a galvanometric frame mirror.

4. The method according to claim 1, wherein optical deflection, injection, focussing and detection means are used having a degree of achromaticity which allows the collection of photons over a whole of an emission band of the excited fluorophore.

5. The method according to claim 1, wherein a quantum efficiency of detection at the fluorescence wavelengths to be detected of at least 50%.

6. The method according to claim 1, further comprising a prior step of detecting a placement of the fibres of the image guide which are intended to be used.

7. The method according to claim 1, further comprising a prior step of determining a real injection rate particular to each fibre.

8. The method according to claim 7, further comprising a prior step of determining a collected flux corresponding to the background image.

9. The method according to claim 8, further comprising a step of correcting a digitized signal coming from a fibre by subtraction of the flux corresponding to the background image and adaptation to the real rate of injection which is particular to said fibre.

10. The method according to claim 9, further comprising by a step of reconstructing an image from the corrected signal.

11. The method according to claim 10, wherein the step of reconstructing the image comprises a Gaussian low-pass filtering.

12. A method for realization of a high resolution fluorescence image, comprising:
    employing an image guide made of several thousands of optical fibres;
    emitting an excitation signal from a continuous source, said excitation signal being deflected and injected by turns into one of the optical fibres of said image guide and a fluorescence signal emitted in response being collected by the same optical fibre as that used for the excitation; and
    detecting and digitizing to form an image element, wherein an end of the fibres is intended to be placed bare directly in contact with a surface of a tissue to be imaged, each fibre being able to produce a divergent beam which is able to excite a microvolume of tissue situated at the surface to a maximum depth depending in particular on a core diameter of the optical fibres and in that the excitation signal is deflected at a speed corresponding to acquisition of a number of images per second sufficient for a real-time use and in that the fluorescence signal is detected at a detection frequency corresponding to a minimum sampling frequency of the fibres one-by-one.

13. An apparatus for in situ and in vivo fibre optic confocal fluorescence imaging, comprising:
    an image guide (6);
    a source (1) emitting continuously at the excitation wavelength of at least one targeted fluorophore,
    means for rapid scanning (4) and injection (5) fibre by fibre over time of an excitation beam produced by the source (1) by lines and by columns in a XY plane corresponding to an entry section of the image guide (6);
    means (3) for separating the excitation wavelength and fluorescence wavelengths;
    means for detection (11) of a fluorescence signal; and
    means (12) for processing the detected signal allowing for realization of an image; and
    an optical head (7) being arranged at a distal end, intended to be brought into contact with an observed tissue (13), allowing the excitation beam to be focused,
    wherein:
    the scanning means are suitable for moving the excitation beam at a speed corresponding to obtaining of an image in real time; and
    the detection means have a pass-band whose frequency is fixed as a function of a minimum one-by-one fibre sampling frequency.

14. The apparatus according to claim 13, wherein the excitation beam produced by the source (1) is a longitudinal monomode beam presenting an optimum wave front quality for injection into a slightly multimode optical fibre.

15. The apparatus according to claim 13, wherein a section of a fibre being circular, the excitation beam produced by the source is circular so as to optimize an injection into a fibre.

16. The apparatus according to claim 13, further comprising means (2) for shaping the beam used on an exit of the source (1) in order to shape the excitation beam so as to adapt the excitation beam to the injection means (5) in the image guide (6).

17. The apparatus according to claim 13, wherein the means for separating the excitation and fluorescence wavelengths comprise a dichroic filter (3) having a maximum efficiency at the excitation wavelength.

18. The apparatus according to claim 13, further comprising rejection means (8) placed upstream of the detection means (11) and suitable for eliminating the excitation wavelength.

19. The apparatus according to claim 13, wherein the scanning means (4) comprise a resonating line mirror (M1), a galvanometric frame mirror (M2), a first afocal optical system (AF1) with unitary magnification adapted for the conjugation of the two mirrors and a second afocal system (AF2) with unitary magnification adapted for the conjugation of rotation planes of the two mirrors with the injection plane in one of the fibres.

20. The apparatus according to claim 13, wherein optical means of the optical head (7), the scanning means (4), the injection means (5) and the detection means (11) present a degree of achromaticity adapted for collection of photons over a whole of a width of a spectral band of the fluorescence signal.

21. The apparatus according to claim 13, wherein the injection means (5) comprise two optical units (E1, E2), the first unit (E1) being adapted for correcting optical aberrations at an edge of a field of the scanning means (4) and the second unit (E2) being adapted for carrying out an actual injection in one fibre of the image guide (6).

22. The apparatus according to claim 21, wherein the first optical unit (E1) comprises a doublet and the second optical unit (E2) comprises two doublets followed by a lens.

23. The apparatus according to claim 13, further comprising a filtering hole (10) placed in front of the detection means (11) whose diameter is chosen so that the image of a fibre fits into said diameter.

24. The apparatus according to claim 23, further comprising means (9) for focussing the fluorescence signal on the filtering hole (10).

25. An apparatus for in situ and in vivo fibred high-resolution confocal fluorescence imaging, comprising:

an image guide (6);

a source (1) emitting continuously at an excitation wavelength of at least one targeted fluorophore, means for rapid scanning (4) and fibre-by-fibre injection (5) of an excitation beam produced by the source (1) in a XY plane corresponding to an entry section of the image guide (6);

means (3) for separating an excitation wavelength and fluorescence wavelengths;

means (11) for detecting a fluorescence signal; and means (12) for processing a detected signal allowing realization of an image;

wherein an end of each fibre is adapted for producing a beam which is divergent and is intended to be placed bare directly in contact with a surface of a tissue to be observed;

and in that the scanning means are suitable for moving the excitation beam at a speed corresponding to obtaining of an image in real time; and the detection means have a pass-band whose frequency is fixed as a function of a minimum sampling frequency of the fibres one-by-one.

* * * * *